United States Patent
Prevelige, Jr.

(10) Patent No.: US 7,297,476 B2
(45) Date of Patent: Nov. 20, 2007

(54) METHOD OF MONITORING HIV ASSEMBLY AND MATURATION

(75) Inventor: Peter E. Prevelige, Jr., Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 397 days.

(21) Appl. No.: 09/800,240

(22) Filed: Mar. 6, 2001

(65) Prior Publication Data

US 2001/0036627 A1 Nov. 1, 2001

Related U.S. Application Data

(60) Provisional application No. 60/186,981, filed on Mar. 6, 2000.

(51) Int. Cl.
*C12Q 1/70* (2006.01)
(52) U.S. Cl. .................................. 435/5; 424/208.1
(58) Field of Classification Search ............ 424/188.1, 424/208.1; 435/5, 69.1
See application file for complete search history.

(56) References Cited

U.S. PATENT DOCUMENTS

| | | | |
|---|---|---|---|
| 5,716,613 A | 2/1998 | Guber et al. | 424/93.2 |
| 5,789,245 A | 8/1998 | Dubensky et al. | 435/320.1 |

OTHER PUBLICATIONS

Murphy, F. A., 1996, "Virus taxonomy", in Fields Virology, Third Edition, Fields, B. N., et al., eds., Lippincott-Raven Publishers, Philadelphia, pp. 15-57.*

Harrison, S. C., et al., 1996, "Virus structure", in Fields Virology, Third Edition, Fields, B. N., et al., eds., Lippincott-Raven Publishers, Philadelphia, pp. 59-99.*

Gross, I., et al., 2000, "A conformational switch controlling HIV-1 morphogenesis", EMBO J. 19(1):103-113.*

Coligan, J. E., et al., 2003, "Strategies of protein purification and characterization", in Current Protocols in Protein Science, Coligan, J. E., et al., eds., John Wiley & Sons, Inc., pp. 1.1.1-1.3.6.*

Zdenek, K., et al., 2004, "Isolation and characterization of the Mason-Pfizer monkey virus p12 protein", Virol. 324(1):204-212.*

Gross, I., et al., 1997, "In vitro assembly properties of purified bacterially expressed capsid proteins of human immunodeficienc virus", Eur. J. Biochem. 249:592-600.*

Trono, D., et al., 1989, "HIV-1 Gag mutants can dominantly interfere with the replication of the wild-type virus", Cell 59(1):113-120.*

Vlasuk, G. P., et al., 1989, "Purification and characterization of human immunodeficiency virus (HIV) core precursor (p55) expressed in *Saccharomyces cerevisiae*", J. Biol. Chem. 264(20):12106-12112.*

(Continued)

*Primary Examiner*—Jeffrey S. Parkin
(74) *Attorney, Agent, or Firm*—Nixon Peabody LLP; Jeffrey A. Lindeman

(57) ABSTRACT

The present invention provides methods to characterize the structure, stability, and intersubunit interfaces between the matrix, capsid, and nucleocapsid domains of the Gag polyprotein during HIV capsid assembly and maturation. A method of screening for compounds that promote or inhibit viral assembly and maturation is disclosed. A novel mass spectrometry based approach to measure hydrogen/deuterium exchange profiles is also disclosed. Quantitative data resulted from these studies may lead to well defined capsid assembly assays that can be adapted for rapid antiviral drug screening.

12 Claims, 8 Drawing Sheets

OTHER PUBLICATIONS

Carolyn M. Teschke et al., Inhibition of Viral Capsid Assembly by 1,1'-Bi(4-anilinonaphthalene-5-sulfonic Acid), Biochemistry 1993, 10658-10665, vol. 32, No. 40.

Ehrlich et al., "*Assembly of Recombinant Human Immunodeficiency Virus Type 1 Capsid Protein In Vitro, Journal of Virology*," vol. 66, p. 4874-4883 (1992).

Coligan et al., "*Strategies of Protein Purification and Characterization*", Current Protocols in Protein Science, 1.1.1-1.3.7 (1995).

Gross et al., "In Vitro *Assembly Properties of Purified Bacterially Expressed Capsid Proteins of Human Immunodeficiency Virus*", European Journal of Biochemistry, vol. 249, pp. 592-600 (1997).

Gross et al., "*A Conformational Switch Controlling HIV-1 Morphogenesis*", The European Molecular Biology Organization Journal, vol. 19, No. 1, pp. 103-113 (2000).

Harrison et al., "*Chapter 3: Virus Structure*", Fields Virology, Third Edition, pp. 59-99 (1996).

Knejzlík et al., "*Isolation and Characterization of the Mason-Pfizer Monkey Virus p12 Protein*", Virology, vol. 324, pp. 204-212 (2004).

Murphy, "*Chapter 2: Virus Taxonomy*", Fields Virology, Third Edition, pp. 15-57 (1996).

Prevelige et al., "*Scaffolding Protein Regulates the Polymerization of P22 Coat Subunits into Icosahedral Shells In Vitro*", Journal of Molecular Biology, vol. 202, pp. 743-757 (1988).

Prevelige et al., "*Nucleation and Growth Phases in the Polymerization of Coat and Scaffolding Subunits into Icosahedral Procapsid Shells*", Biophysical Journal, vol. 64, pp. 824-835 (1993).

Prevelige et al., "*Inhibiting Virus-Capsid Assembly by Altering the Polymerisation Pathway*", Tibtech, vol. 16, pp. 66165 (1998).

Spector et al., "*The Post-Polio Syndrome: Current Concepts and Treatment*", Infections in Medicine, pp. 462-478 (1997).

Tang et al., "*Antiviral Inhibition of the HIV-1 Capsid Protein*," J. Mol. Biol. 327, 1013-1020 (2003).

Trono et al., "*HIV-1 Gag Mutants Can Dominantly Interfere with the Replication of the Wild-Type Virus*", Cell, vol. 59, pp. 113-120 (1989).

Vlasuk et al., "*Purification and Characterization of Human Immunodeficiency Virus (HIV) Core Precursor (p55) Expressed in Saccharomyces cerevisiae*", The Journal of Biological Chemistry, vol. 264, No. 20, Issue of Jul. 15, pp. 12106-12112 (1989).

\* cited by examiner

METHOD OF MONITORING HIV ASSEMBLY AND MATURATION

CROSS-REFERENCE TO RELATED APPLICATION

This non-provisional patent application claims benefit of provisional patent application U.S. Ser. No. 60/186,981 filed Mar. 6, 2000, now abandoned.

BACKGROUND OF THE INVENTION

1. Field of the Invention

The present invention relates generally to the fields of biophysics and virology. More specifically, the present invention relates to detailed biophysical studies which will lead to both a quantitative understanding of HIV assembly and maturation, and the development of in vitro assays that can be readily adapted for drug screening and evaluation.

2. Description of the Related Art

HIV-1 (and retroviruses in general) assembles through the controlled polymerization of the Gag polyprotein. The Gag polyprotein is transported to the plasma membrane and forms patches within which assembly occurs (1). Transport to the plasma membrane acts to concentrate the Gag protein but is apparently not essential as Gag protein expressed at sufficiently high levels is capable of cytoplasmic assembly (2). During assembly, the patches enlarge and bud outward ultimately pinching off from the cell. During budding, the virion acquires the envelope proteins necessary for receptor binding, as well as a lipid envelope.

Morphologically, the released immature virion presents as an enveloped particle approximately 100 nm in diameter, containing a spherical core (3). The viral protease is incorporated into the virion as part of a Gag-Pol fusion protein, arising from a −1 translational frameshift. Budding activates the protease, which cleaves the Gag polyprotein into the matrix (MA), capsid (CA), and nucleocapsid (NC) domains as well as the "spacer" peptides P2, P1, and the C-terminal P6 domain. The immature virion is metastable, and cleavage of the polyprotein is associated with a profound morphological change in the virion (4). The matrix domain stays associated with the membrane envelope, the capsid domain collapses to form a conical core, and the nucleocapsid domain condenses with the viral RNA in the center of the conical capsid core. The structural rearrangements necessarily arise from the disruption of existing interdomain contacts and the formation of new ones (FIG. 1).

Despite a wealth of structural information about the isolated HIV-1 matrix, capsid, and nucleocapsid domains, little is known about the structure and interactions of these elements within either the immature or mature virus. The structure of the domains themselves may be different in the context of the full length Gag polyprotein than in isolation. The intersubunit interfaces between the domains which promote assembly and their changes upon maturation have not been identified.

Nothing is known of the nature of the large scale motions within the virion required for protease access, maturation, and uncoating. There are two reasons why this is so: the enveloped, non-icosahedral, pleomorphic nature of the virion makes cyrstallographic analysis of the intact virion nearly impossible, and techniques to study the dynamics of large protein complexes have not been readily available.

The prior art is deficient in the lack of detailed quantitative information on the protein/protein interactions mediating HIV assembly and maturation. The present invention fulfills this long-standing need and desire in the art.

SUMMARY OF THE INVENTION

The present invention is drawn to methods to characterize the structure, stability, and intersubunit interfaces between the matrix, capsid, and nucleocapsid domains of the Gag polyprotein in virus-like particles. The present invention features studies on HIV-1 in particular. Although high resolution structures are available for all three of these domains, the structural determinations have been performed on isolated domains, and the relationship between these domains in the virus is unknown and difficult to determine by traditional methods.

The present invention provides a method to monitor the kinetics of in vitro capsid protein (CA) assembly. In these studies HIV-1 capsid protein was assembled by diluting in concentrated NaCl to produce a final concentration of 1 M NaCl instead of dialyzing capsid protein into 1 M NaCl, thus allowing rapid transfer of the assembly reaction to the cuvette for analysis. The capsid protein assembly rate was dependent on capsid concentration and the capsid protein C-domain interactions. Analyzing the kinetics of capsid assembly provides a sensitive method for monitoring and screening mutations and inhibitory compounds that modulate capsid-capsid protein interactions involved in assembly.

The present invention also provides a novel mass spectrometry based approach to measure hydrogen/deuterium exchange profiles is used to identify intersubunit interfaces and characterize domain stability. This is complemented with Raman spectroscopy-based studies of subunit structure and stability. Selected wild type and mutant proteins which have been shown to polymerize into physiologically relevant forms are characterized and then use this information to characterize mature and immature enveloped virus-like particles budded from cells grown in culture. These studies provide otherwise unobtainable information on the interactions between the structural domains of HIV-1. The significance of this work is that these steps: assembly, protease activation, maturation, and uncoating are critical to the HIV lifecycle and represent either potential or actual (i.e., protease inhibitors) therapeutic targets. Fully exploiting the potential of these interactions as targets requires a detailed understanding of their form, strength, stability and rate of formation. The present biophysical studies may also result in the development of simple, rapid, and well defined assays for capsid assembly which can be then adapted for rapid antiviral drug screening.

In one embodiment of the invention, there is provided a method of screening for compounds that promote or inhibit viral assembly and maturation comprising the steps of: maintaining viral structural protein in a soluble form; triggering assembly of said viral protein; contacting said buffer containing said viral protein with a candidate compound or a control compound that does not inhibit viral assembly; and monitoring viral assembly.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
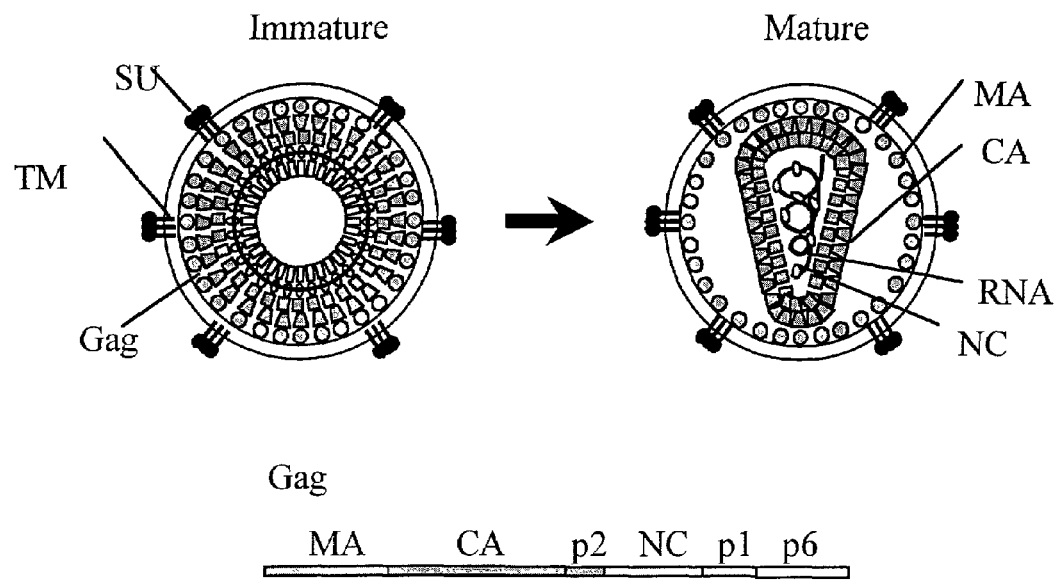
FIG. 1 shows HIV capsid assembly. The Gag polyprotein precursor assembles at the cell membrane and subsequently buds to release an immature viral particle. The Gag polyprotein is then cleaved by the protease releasing the matrix (MA), capsid (CA), nucleocapsid (NC) proteins and the P2, P1, and P6 peptides. The released capsid and nucleocapsid proteins condense forming a conical core while the MA protein remains associated with the membrane.

This invention encompasses a method for detailed biophysical characterization of HIV capsid assembly using spectroscopic and hydrogen/deuterium (H/D) exchange studies. Hydrogen/deuterium exchange studies provide a powerful means of identifying structural elements in proteins and assemblies. The exchange rate of the amide protons of the polypeptide backbone can vary over five orders of magnitude depending upon whether the amide proton of interest is in a solvent exposed peptide, or buried in the folded core of a protein (5,6). In proteins and structured polypeptides, the amide protons are exchange protected by hydrogen bonding within α-helices and β-sheets. Further protection is afforded by the hydrophobic core in globular proteins (7). As a result, the limiting step of hydrogen exchange is the formation of an open, exchange competent state (8,9). The rate of open state formation depends on solvent accessibility and local and global stability. Protein/protein interactions within and between protein subunits can increase local and global stability and thereby retard the rate of hydrogen/deuterium exchange. Regions which interact to form cooperative folding and association units can be determined by identifying correlations between regions with regard to the temperature dependence of exchange (10,11). Because every amino acid (except proline and the N-terminal amino acid) carries an amide proton, hydrogen/deuterium exchange provides a probe of the local environment of every amino acid within a protein.

Two recently developed techniques can be used to manipulate hydrogen/deuterium exchange as applied to virus capsids. The first, a Raman spectroscopic probe of hydrogen/deuterium exchange, takes advantage of the fact that the frequencies of the vibrational modes decrease when a deuteron replaces the amide proton (12). This results in an easily monitored shift of the Raman bands, which can be assigned to elements of secondary structure. This technique provides information about overall exchange rates, and the elements of secondary structure that are exchanging. A complementary technique is hydrogen/deuterium exchange as detected by mass spectrometry. The strategy in using mass spectrometry to measure hydrogen/deuterium exchange is to exchange the protein or protein complex of interest under a defined set of conditions. During this interval, the exchange rate is determined by the protein structure and dynamic behavior. The protein is then digested under acidic conditions to yield small (10-15 amino acid) peptides whose mass and position within the primary sequence can be accurately determined (13-17). Quantification of the increase in mass arising from replacement of the amide protons by deuterons yields the degree of hydrogen/deuterium exchange. This technique yields information about the exchange rate of individual peptide fragments but cannot directly determine changes in secondary structure.

The present invention features a method of screening for a compound or viral protein mutant that promotes or inhibits viral assembly and maturation comprising the steps of: maintaining viral structural protein in a soluble form; triggering assembly of said viral protein; contacting said viral protein with a candidate compound or a control compound that does not inhibit viral assembly; and monitoring viral assembly. Preferably, the viral assembly and maturation is HIV-1 assembly and maturation. Representative viral structural protein include matrix protein, capsid protein, nucleocapsid protein and gag protein of HIV-1.

Preferably, viral structural protein is maintained in a soluble form through the use of pertubant. In one embodiment, the perturbant is NaCl. The NaCl would be so used in a concentration of from about 1 M to about 4 M. In another embodiment, the perturbant is GuHCl. The GuHCl would be so used in a concentration of from about 1 M to about 6M. Preferably, the assembly of viral protein is triggered by rapid removal of pertubant, e.g., by dilution. This method can be used to evaluate various candidate compounds such as protein, peptides derived from the HIV gag polyprotein and non-peptide mimics of those peptides. The viral assembly can be monitored by measuring turbidity, fluorescence or physical separation of the polymerized materials. Furthermore, one may use techniques for detecting subunit/subunit interactions suitable for high throughput screening.

In another aspect, the invention features a method to optimize digestion conditions and assign peptides spanning the Gag polyprotein.

In yet another aspect, the invention features a method to determine the alterations in the exchange protection profile of the Gag polyprotein and its domains accompanying polymerization.

The invention also features a method to determine the dynamic stability of spherical and cylindrical polymers.

The invention further features a method to characterize the domain interactions within mature and immature budded viral particles.

The following examples are given for the purpose of illustrating various embodiments of the invention and are not meant to limit the present invention in any fashion.

EXAMPLE 1

Purification of HTV-1 Structural Proteins

Coding sequences for capsid protein (CA), full length Gag protein, capsid protein with the four C-terminal matrix residues fused ($MA_4$-CA), and a mutant of the capsid protein (M185A), which cannot form the C-terminal dimeric interface and therefore forms long strings rather than cylinders (18), were cloned into pET-based expression vectors and transformed E. coli BL21 (DE3). The Gag expressing cells also carried a plasmid encoding dnaY gene which supplies a minor Arg tRNA and results in increased expression (19). The cells containing plasmids expressing capsid and capsid variants were grown and induced with IPTG according to standard procedures. After three hours the cells were lysed with the addition of lysozyme, the lysate sonicated and clarified by low speed centrifugation. The capsid proteins were precipitated by the addition of ammonium sulfate, resuspended and dialyzed into 25 mM KMOPS pH 6.9 buffer and purified by Q-sepharose ion exchange chromatography.

Cells expressing the his-tagged Gag protein were grown and induced as described above. The Gag protein forms inclusion bodies, and therefore had to be maintained in a soluble form for purification by the addition of denaturant. The cells were lysed in the presence of 6 M GuHCl and incubated overnight. Cell debris was pelleted with a low speed spin, and the protein was bound to a charged nickel column (Qiagen) in 6 M GuHCl and extensively washed in 6 M GuHCl containing buffer. While the Gag protein remained bound to the column the GuHCl was exchanged by washing with 8 M urea. The bound Gag protein was released from the column by acidification to pH 3.5 with sodium phosphate buffer. The released Gag, in the presence of 8 M urea, was neutralized by the addition of 1 M Tris-HCl pH 9 and applied to a n SP-Sepharose ion exchange chromatography. The Gag protein passed through the column while contaminating proteins remained bound. Removal of the urea from purified Gag by dialysis into 50 mM NaCl, 25 mM Tris, pH 7.6 resulted in aggregation. Therefore, the protein was stored in denaturing concentrations of urea.

E. coli BL21 (DE3) cells carrying a pET based clone expressing the CA-NC and CA-NC-p6 domains were induced and the protein purified as described (20).

While the analyses of Gag structures assembled in vitro will yield significant new information on Gag protein structure and assembly, such in vitro made structures may not be accurate reproductions of those that are budded from cells. One of the advantages of the hydrogen/deuterium exchange technology is that the presence of lipids does not affect the ability of the assay to examine proteins since membranes are permeable to $D_2O$. Thus it is possible to directly probe the structure of enveloped particles produced from cells. Furthermore, since the HIV protease can be easily inactivated by the introduction of a mutation into its active site sequence, it is possible to produce and therefore examine both morphologically mature and immature particles.

To produce such particles, the Tet-Off™ expression system (CLONTECH™) was used to express gag-pro in tissue culture cells. PCR primers PNL4GAGSacII and PNL4PRSTOP were used to amplify the sequence from the infectious molecular HIV clone pNL4-3 to generate wild-type gag-pro. For the introduction of the D25N mutation into the protease sequence two additional primers, PNLMFED25NPR and PNLMFED25NGAG, were used.

EXAMPLE 2

Assembly of HTV-1 Capsid Protein

The HIV-1 capsid (CA) protein plays a crucial role in both assembly and maturation of the virion. The present invention develops a method for monitoring capsid assembly to characterize capsid-capsid interactions involved in capsid assembly. Monitoring the process of polymer assembly with kinetic analysis has been well established for many years. The in vitro assembly of the Tobaco Mosaic virus was the first to be studied with kinetic analysis. Similar techniques have also been applied to the assembly of P22 in order to elucidate key steps in the assembly process. Analyzing the kinetics of capsid assembly provided a sensitive method for monitoring the effects of capsid mutations and inhibitory compounds on capsid-capsid protein interactions involved in assembly.

A dilution technique was developed to trigger capsid assembly instead of dialysis into 1 M NaCl in order to rapidly transfer the assembly reaction into the ultraviolet (UV) light spectrometer cuvettes for analysis. The proteins were dialyzed into 50 mM $Na_2HPO_4$ at pH 8.0 and the capsid protein was concentrated to 1 mM. The capsid protein was then diluted with 50 mM $Na_2HPO_4$ at pH 8.0 to give the final concentration necessary for the assembly reaction at a volume of 197 uL. The capsid protein was triggered to polymerize by the addition of 197 uL of 50 mM $Na_2HPO_4$ 4 M NaCl at pH 8.0 to produce a final 2.25 M NaCl concentration. Initial assembly reactions were done using a final 1 M NaCl concentration. Following the addition of NaCl the assembly reaction was rapidly mixed and place into a cuvette.

Approximately 20 sec elapsed between when capsid protein was triggered to assemble and the first time point was monitored. The assembly of capsid protein into larger polymers was followed as an increase in optical density. The large polymers formed during capsid assembly caused an increase in light scattering that was observed as an increase in the solutions turbidity (optical density). The increase in optical density was monitored on a spectrometer at 350 nm every 20 sec for 0.5 sec. The data points representing the largest increase in optical density were linear fit using the origin fitting program to obtain the slope of the line tangent to these data points. For the assembly reactions with either the N-domain or C-domain present they were mixed with the fulllength capsid protein prior to triggering assembly.

Figure 2:
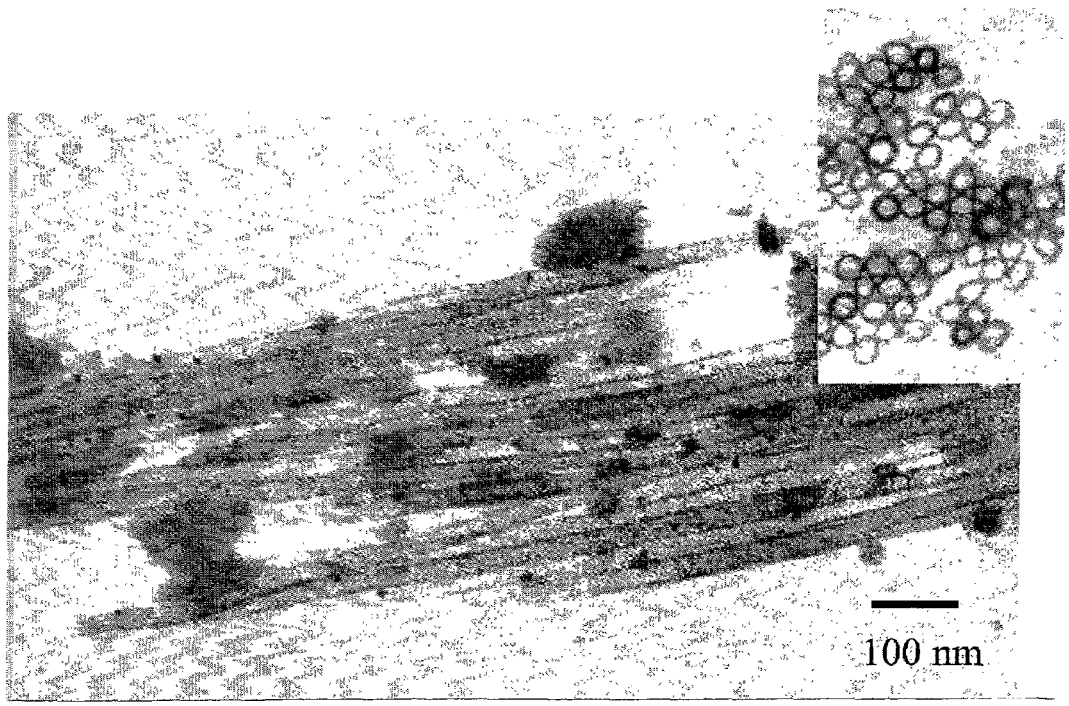
FIG. 2 shows thin section EM analysis of polymerized capsid (CA) protein formed with dilution technique. A stock solution of capsid protein was diluted to a final concentration of 350 µM capsid protein in 1 M NaCl. Thin section TEM showed that the polymerized capsid protein had formed cylinders similar to those previously observed. The inset show end on views of the approximately 33 nm diameter tubes. Thus, dilution into high salt produces biologically relevant structures.
Figure 3:
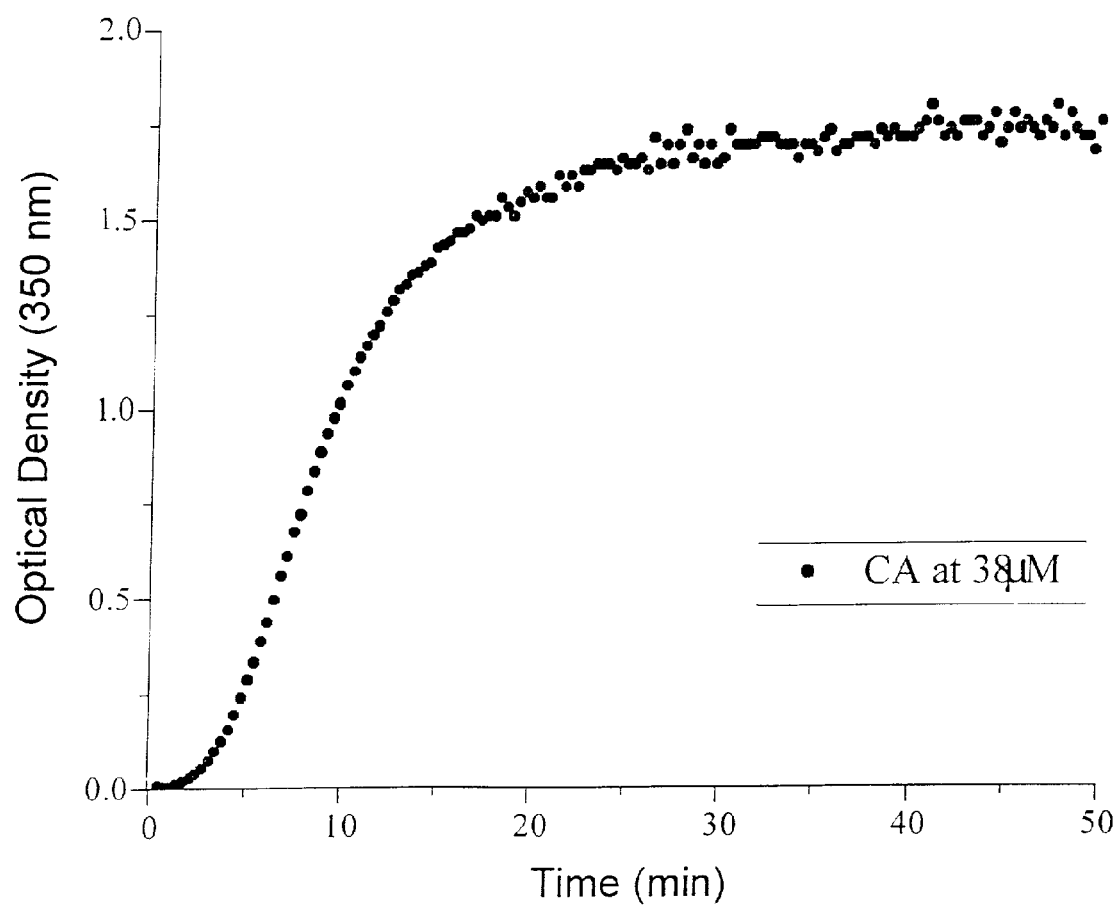
FIG. 3 shows salt induced polymerization of capsid protein at 38 µM.

CA protein was assembled at a final 350 uM capsid protein concentration and final 1M NaCl concentration. The capsid assembled at 350 µM was collected by centrifugation and observed by thin-section transmission electron microscopy (TEM) to have formed long hollow cylinders similar to the polymers observed previously (FIG. 2). The end on view shows that the cylinders had a diameter similar to that reported by Schwedler et al (ca. 33 nm). Capsid could also be triggered to assemble polymers at lower protein concentrations when a higher NaCl concentration (2.25 M NaCl) was used. The oligomers formed at lower capsid concentrations were bunched together making it difficult to observe individual cylinders with thin-section TEM. The cylinders observed in the micrographs for capsid assembly at 38 µM also had a similar diameter to the capsid protein assembled at 350 µM. This suggested the capsid-capsid interactions formed during capsid assembly at 350 µM were similar to the interactions formed at 38 µM and the latter concentration could also be used for studying interactions involved in capsid assembly (FIG. 3).

Figure 4:
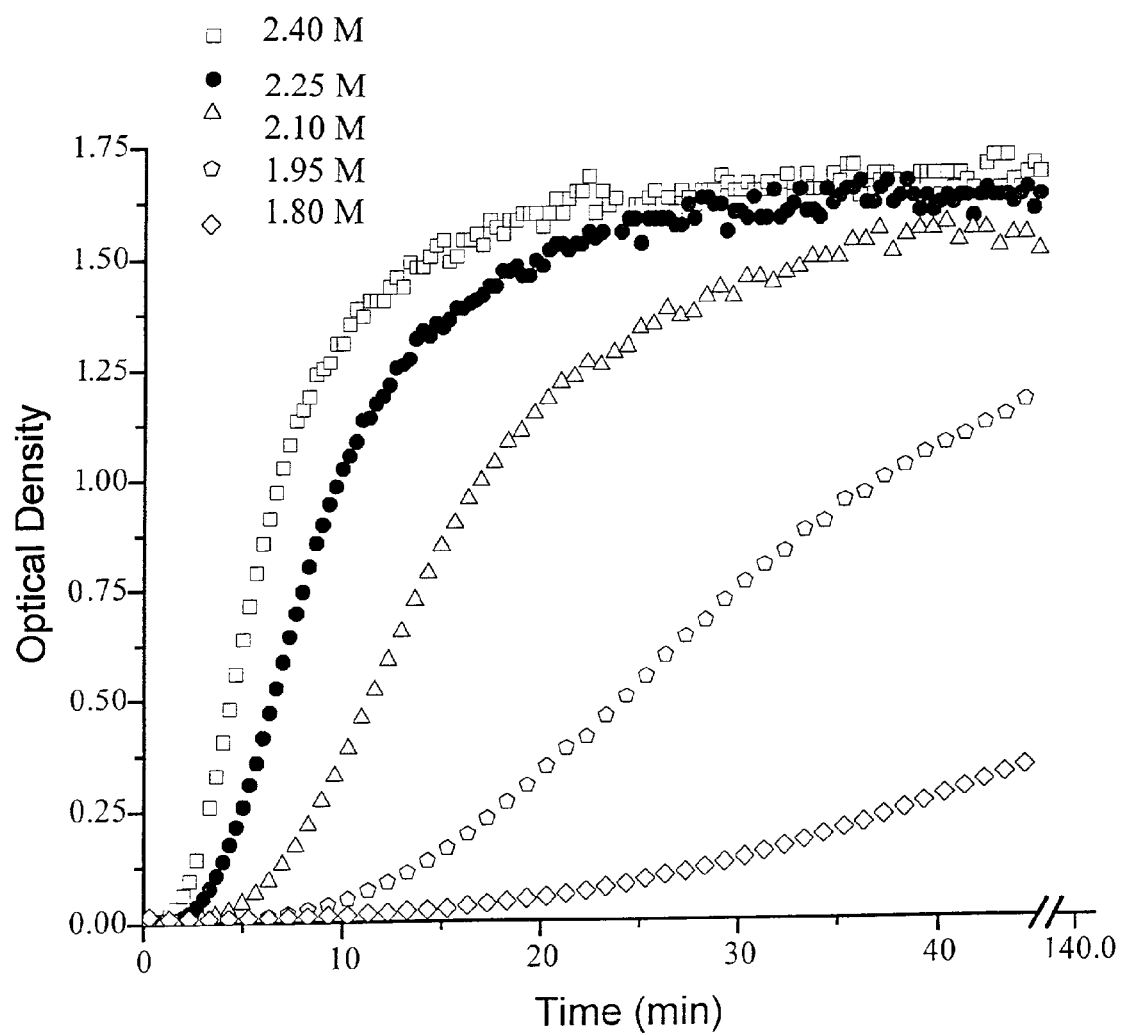
FIG. 4 shows the rate of assembly increases with salt concentrations. CA was diluted to final salt concentrations ranging from 1.8 to 2.4 M NaCl. There was a pronounced effect of salt on the rate of assembly. However, the final amount of turbidity achieved at extended period of time (140 min) was relatively independent of the salt concentrations, suggesting that salt increases the rate of assembly rather than the fraction of capsid protein capable of assembly.

The assembly rate of capsid protein was affected by the salt concentration used. As shown in FIG. 4, there was a pronounced effect of salt on the rate of assembly. However, at extended period of time (140 min), the final amount of turbidity achieved was relatively independent of the salt concentrations, indicating that the salt increases the rate of assembly rather than the fraction of capsid protein capable of assembly. A final 2.25 M NaCl concentration was used to trigger assembly of capsid mutant M185A (150 µM) to assemble on a time scale of minutes and a lower capsid (38 µM) concentration could be used to keep the spectrometer from being saturated. The capsid protein mutant M185A required a concentration approximately three times higher then capsid to assemble on the same time scale (data not shown). Similar to the change in morphology caused by M185A mutation, this decreased rate of assembly reflected the loss of capsid-capsid interactions necessary for assembly.

Capsid was assembled at different protein concentrations to determine the effect concentration had on assembly rates. A small concentration range of 56 µM to 26 µM showed the assembly rate is strongly dependent on capsid concentration. The region of large increase in turbidity was linearly fit to obtain the assembly rate. The slope for this line represents the rate for assembly. The rate verse the capsid concentration demonstrates the dependence on capsid concentration.

Figure 5:
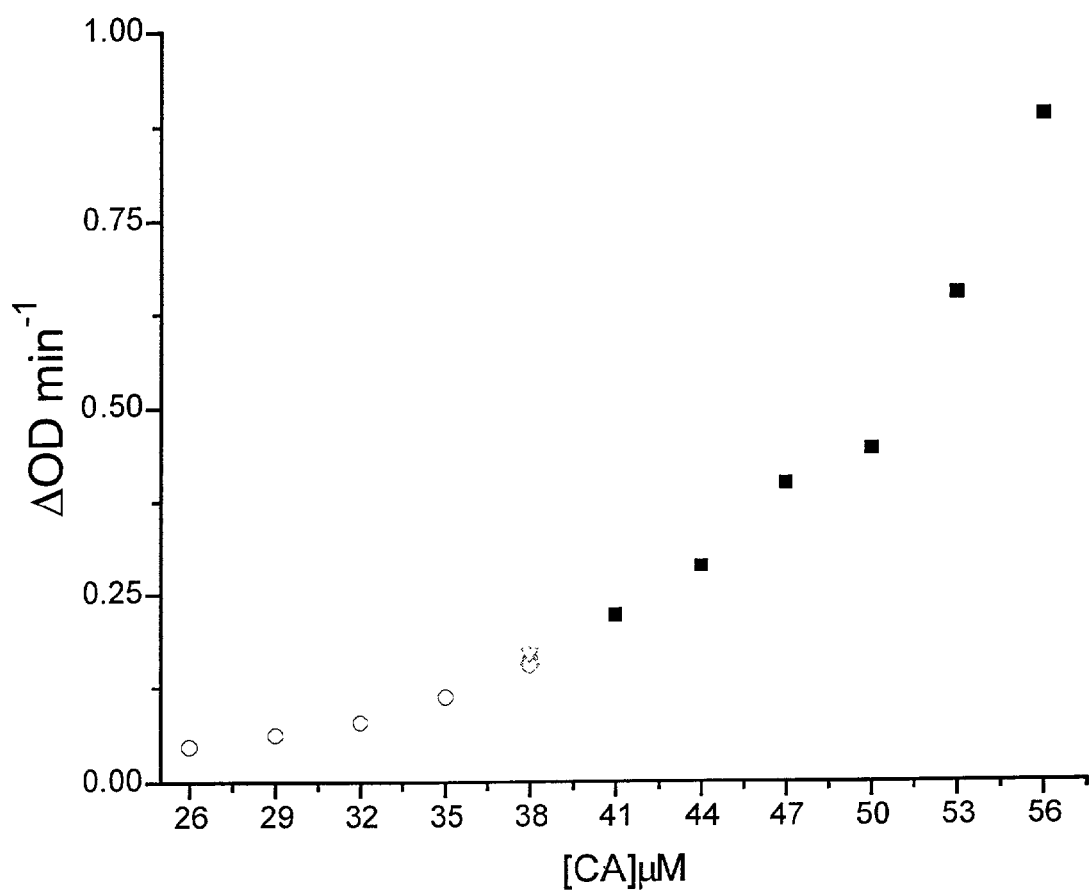
FIG. 5 shows the measured assembly rates are reproducible. The data plotted in open circles and solid squares represents data collected in two different assembly reactions. The superimposed data points at 38 µM represent five different capsid assembly reactions, thus indicating that the assembly rates for capsid are reproducible. These data also indicate the strong concentration dependence of capsid assembly.

The data plotted in open circles and solid squares in FIG. 5 represent data collected in two different assembly reactions. The superimposed data points at 38 82 M represent five different capsid assembly reactions, indicating that the assembly rates for capsid are reproducible. These data indicate that the present invention is able to monitor capsid polymerization kinetics and the rates reflect capsid-capsid interactions.

Figure 6:
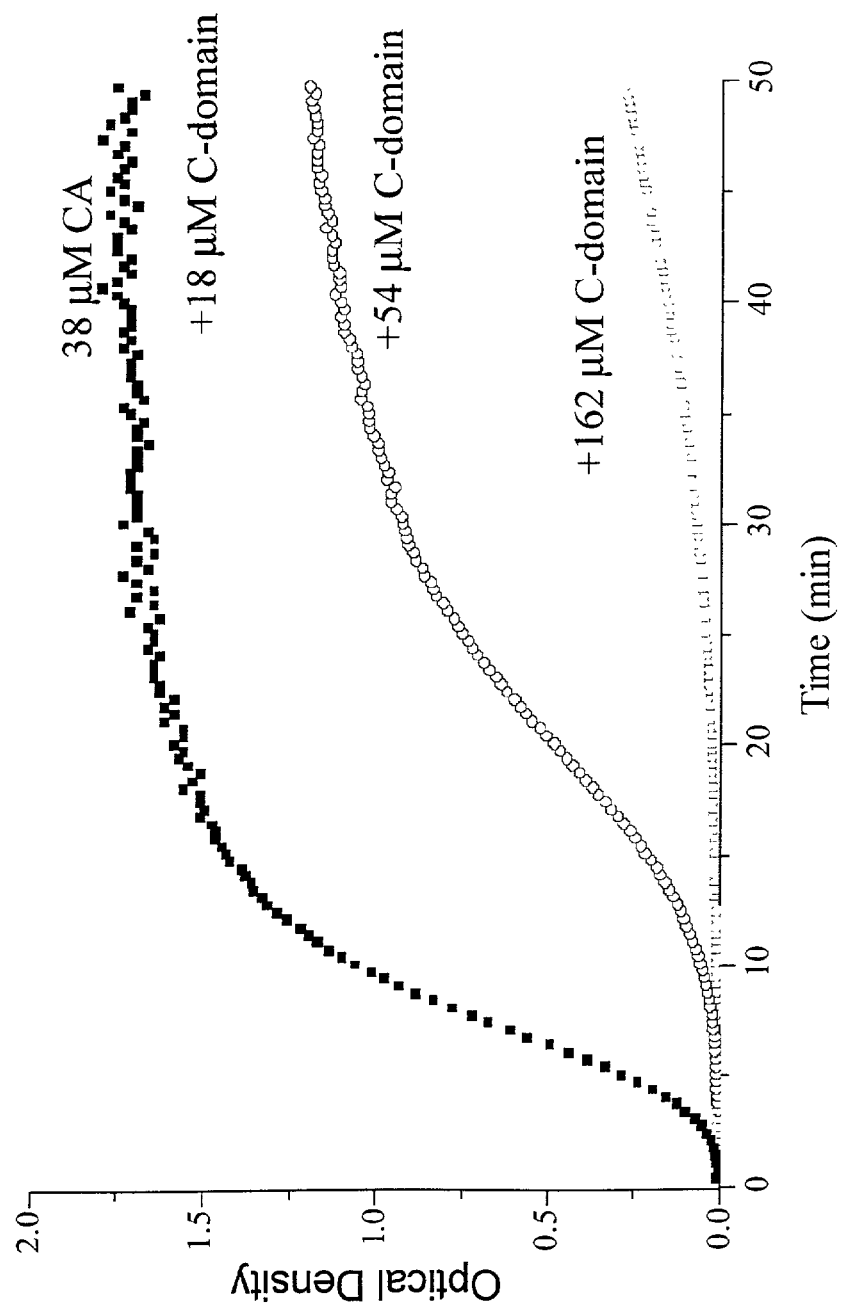
FIG. 6 shows the C-domain inhibits capsid assembly. Addition of the C-terminal domain of the HIV-1 Capsid to assembly reactions results in inhibition of assembly. This provides proof of principle for the ability of this assay to detect inhibitors of assembly.
Figure 7:
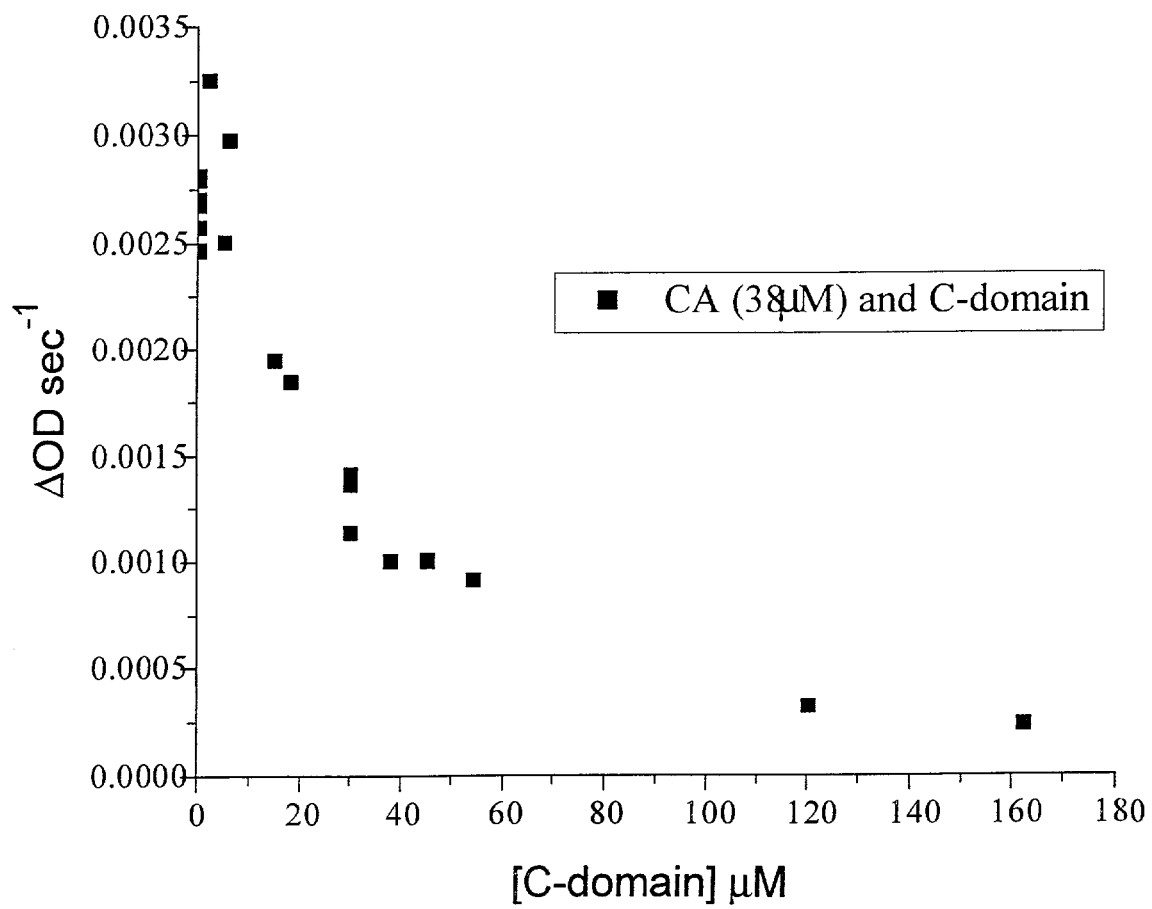
FIG. 7 shows the C-domain inhibits capsid assembly by forming CA-C-domain heterodimers. The effect of added C-terminal domain on the rate of assembly was evaluated by plotting the rate of assembly versus C-terminal domain concentration. The inhibition increased with increasing C-terminal domain in an exponential rather than linear manner, and no threshold concentration for inhibition was observed. Taken together these data suggest that the C-terminal domain inhibits assembly through the formation of a biologically inactive heterodimer.
Figure 8:
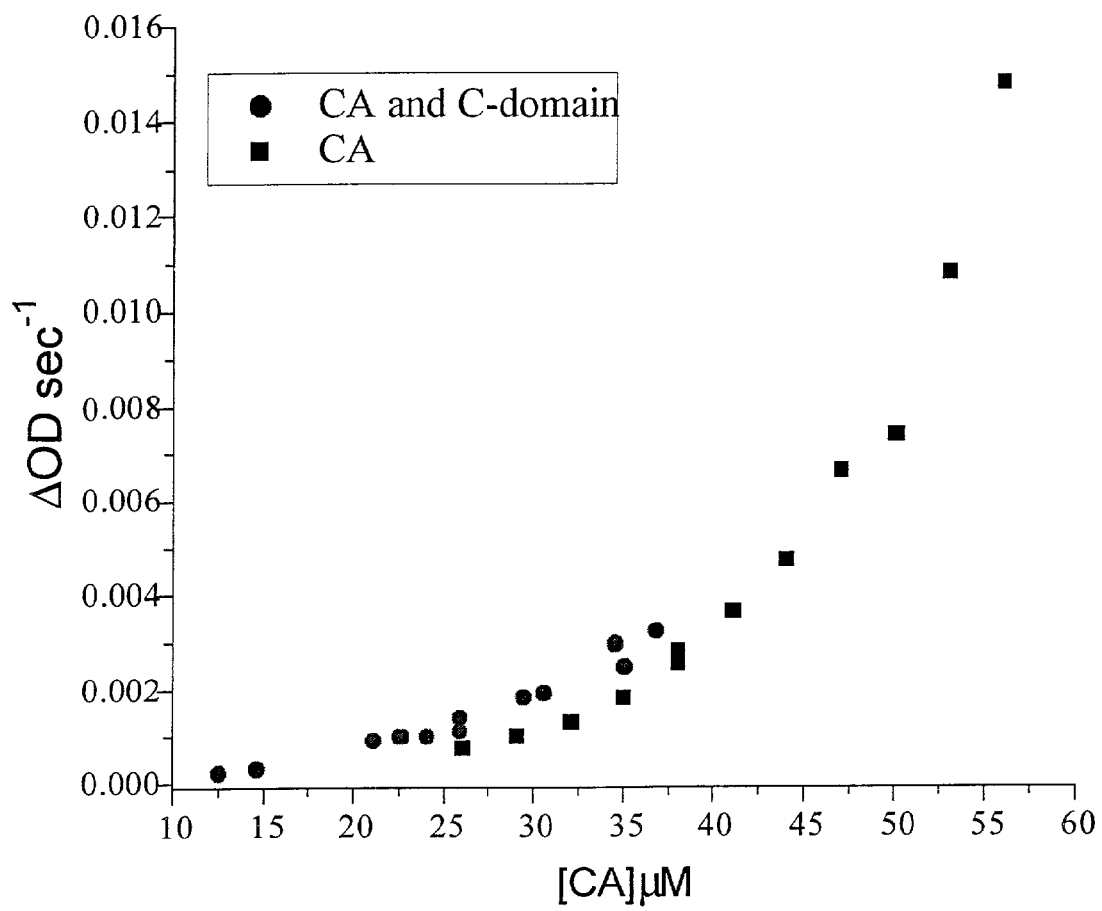
FIG. 8 shows the C-domain decreases the effective concentration of capsid. The squares are the data for capsid assembly. The circles are the data for the effective concentration of capsid free to participate in assembly. The effective capsid concentration was determined by subtracting the heterodimer concentration from the capsid concentration. The heterodimer concentration was calculated based on the known association constant.

The known capsid C-domain dimerization interface was an obvious choice to test if blocking CA-capsid interactions would disrupt assembly. Capsid and C-domain were mixed prior to assembly, and the assembly rate was decreased (FIG. 6). The decreased rate of capsid assembly was concentration dependent on C-domain. The capsid rates verse the C-domain concentration shows an exponential dependence on C-domain concentration (FIG. 7). The most probable mechanism for C-domain inhibition is through capsid inactivation by formation of capsid and C-domain heterodimers.

The capsid C-domain heterodimer concentration present in solution prior to assembly was determined using the capsid dissociation constant (10 mM) and C-domain dissociation constant (18 mM) average (14 mM). The capsid concentration minus the heterodimer concentration (effective capsid concentration) was taken to be the capsid concentration free in solution to participate in assembly. When the capsid assembly rates were plotted verses their effective capsid concentration, they aligned very close to the assembly rates in the presence of capsid alone. These data are in agreement with the notion that the C-domain inhibits capsid assembly by the formation of heterodimers.

Another capsid interaction necessary for assembly is the proposed N-domain interactions responsible for formation of the capsid hexamers. The N-domain and capsid were mixed together prior to assembly to determine if the N-domain would affect capsid assembly. Although the N-domain interactions would be expected to be essential to capsid polymer formation, capsid assembly was not affected by the addition of N-domain (data not shown).

To determine whether the C-domain and N-domain interact to change the capsid assembly rates, C-domain and N-domain were mixed with capsid prior to assembly. The N-domain was found to partially alleviate the C-domain inhibition. Presumably the N-domain interacts with the C-domain to interfere with the interactions necessary for C-domain inhibition. Assembly with the N-domain and C-domain added separately or combined together showed no increase in turbidity. Thus the change in optical density with time was not due to an inherent effect of the N- and C-domain but instead was due to an effect they have on capsid assembly.

These data suggest that the N-domain interacts with capsid or the C-domain. Amine to amine cross-linking was used to determine if the N-domain was interacting with the C-domain. The N-domain and C-domain (45 µM for both) were mixed together with a final 2.25 M NaCl concentration. In addition to the C-domain and N-domain homodimers that were detected by SDS-PAGE, a C-domain and N-domain heterodimer was also observed, supporting the idea that the N- and C-domain were interacting.

Figure 9:
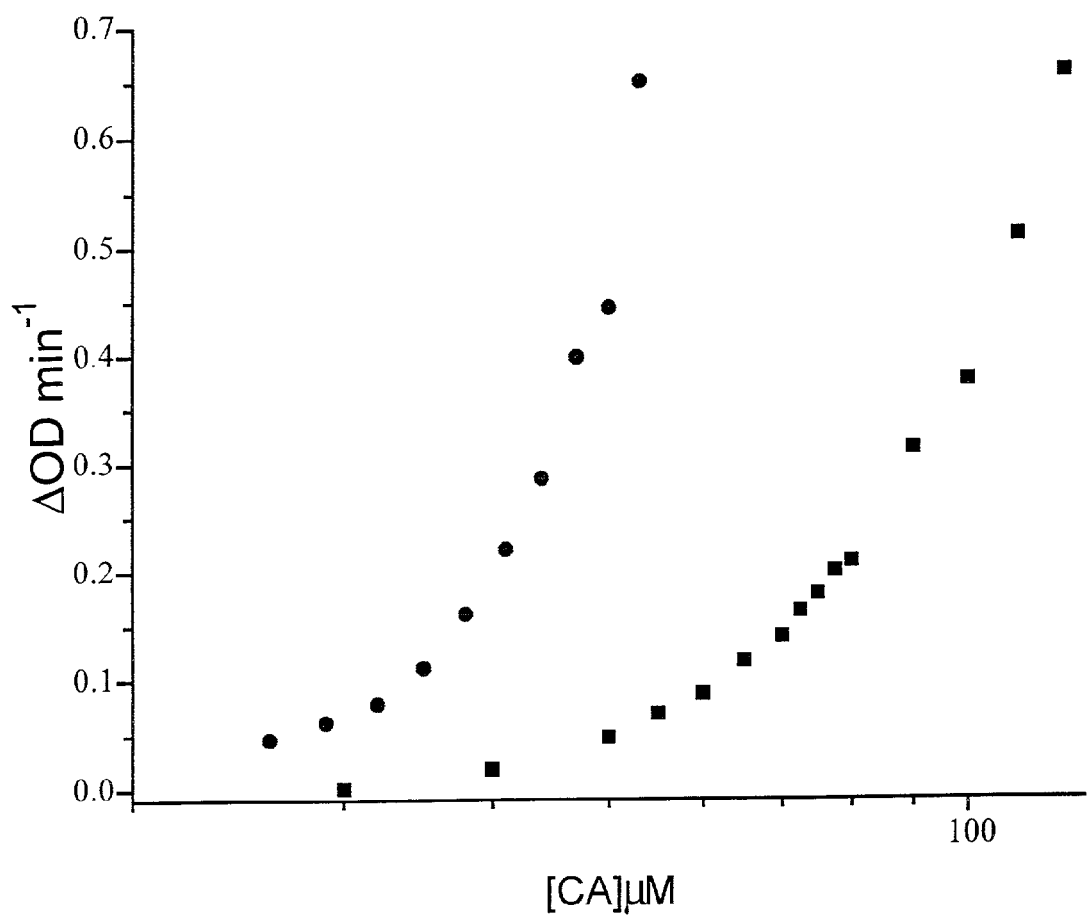
FIG. 9 shows mutations alter the assembly rate. The assembly rates shown are for the wild type capsid (circles), the mutant capsid proteins E128A(triangles) and M185A (squares). The effects of mutations which either increase or decrease subunit interaction can be detected. Similar analysis is extendable to external modulators of subunit/subunit affinity.

The assembly assay described above can also be used to examine the effects of capsid mutations on capsid assembly. As shown in FIG. 9, the effects of mutations which increase or decrease subunit interaction can be detected. Similarly, the assay can be extended to examine the effects of external modulators that modulate subunit interactions.

Discussion

Cryo-electron microscopy showed the capsid cylinders were constructed with a hexamer lattice, where hexamer rings were connected to adjacent rings by density regions protruding from the rings. In these density maps the crystal structure of the capsid N-domain packed best into the density region forming the hexamer ring. A N-domain would form interactions with the N-domains adjacent to it through helices one and two. Repetition of these N-domain interactions formed a hexamer ring, and these rings were tethered together by the C-domain that packed best to the density region between these hexamer rings. This C-domain interaction was observed in the crystal structure where the C-domain crystallized as a dimer. A methionine to alanine mutation at this dimerization interface (residue 185) caused the capsid protein to form no detectable dimers when observed with equilibrium analytical ultracentrifugation. Both the N-domain and C-domain interactions described above are then propagated to form the hexamer lattice of the cylinder. The same hexamer lattices observed in the cryo-EM reconstructions were modeled to form conical cones with angles similar to those observed in the viral conical core. These data suggest the in vitro assembled capsid cylinders are valid models for studying the CA-capsid interactions involved in conical core formation.

In addition the cryo-EM data above, the in vitro assembled capsid makes a good system for studying the capsid-capsid interactions involved in forming the conical core because the recombinant capsid protein can be produced in large quantities, the capsid protein can be triggered to assemble in vitro, and the in vitro assembled capsid polymers are more amenable to structural studies. Most studies done with in vitro assembled capsid had focused on the effects mutations had on the morphology of the polymer or the solution state of the capsid protein. These data had provided insight into both the capsid starting state and the assembly end product. However, no studies have focused on the process of assembly.

CA polymerization into cylinders involves many complex interactions that can be studied through assembly kinetics. The present invention provides a method of capsid assembly that represents capsid-capsid interactions similar to those observed in the virus. During the assembly process, the increase in NaCl concentration causes capsid to form the proper interactions necessary to form hexamers and these interactions are propagated to form cylinders.

However, not all of the capsid protein assembled into cylinders. Some capsid remained in solution, and capsid that was in oligomers smaller then 24S was not pelleted, suggesting that there is a critical concentration for capsid to assemble. Another portion of the capsid formed clumps of aggregates of some form that could be observed by TEM. These clumps probably are not nonspecific aggregates. Nonspecific aggregates are usually associated with a change in secondary structure; however, there was no difference in secondary structure between soluble capsid and assembled capsid when analyzed with Raman spectroscopy (data not shown).

The N-domain and C-domain either separately or mixed together did not assemble into oligomers when monitored with turbidity, suggesting the NaCl-induced assembly of capsid oligomers requires specific interaction of both the N-domain and the C-domain in the intact capsid protein. This indicates that the capsid protein was assembling through only specific interactions and not nonspecific aggregates. The requirement for specific interactions of both domains suggests the assembled capsid consists of cylinders and aberrant species that are formed with similar capsid-capsid interactions as the cylinders. The pathway of assembly could be considered similar to that of protein folding. At the start of assembly the capsid proteins primarily exists as a dimer or monomer in equilibrium. Following the addition of NaCl, the capsid protein forms intermediates that will progress to form larger polymers. Similar to protein folding the assembly falls off during the formation of intermediates. The capsid protein primarily aggregates to form three final species: the conical core, the cylinders or the aberrants. Slight variances in the global conformation of these intermediates could be reflected in the formation of aberrants, cylinders, or conical cores.

The curvature at different positions in the hexamer lattice in the cylinders will be different depending on how the capsid protein aligns with the lattice. Adopting a curvature that is slightly unfavorable could destine the two sides of the cylinder to not meet and progress into an aberrant as more capsid protein was bound to the intermediate. The capsid protein must also form slightly different angles within the hexamer lattice to form the conical core. The inherent flexibility capsid protein relative to each other allows it to use a similar lattice to form both cylinders and tubes. The aberrants probably form when the intermediates are forming angles specific to cylinders and some of the capsid proteins form angles involved in forming the core. The incompatibility of the two forms causes the formation of the aberrant species.

The kinetic analysis of capsid assembly can be used to study changes in capsid-capsid interactions through mutations or through inhibitors. The effects of mutations on the assembly rate were observed with the M185A mutation which required a concentration approximately three times higher than wild type capsid to produce a similar rate for assembly. This dramatic decrease in assembly reflects the decreased interaction at the capsid dimerization interface. However, the decreased but not absence of assembly suggests that some of the interactions necessary for assembly are still present in M185A. Further studies of M185A assembly may reveal differences in the assembly process for capsid and M185A. Sundquist and coworkers have suggested the C-domain interaction functions to tether together the hexamer units formed from the N-domain. If the C-domain functions just as a tether, it should not affect morphology unless the capsid dimers are limiting to the assembly process.

The C-domain was used to test the ability of the kinetic analysis to detect inhibition. The present invention demonstrated that the inhibition of capsid assembly by the C-domain is related to the ability of the capsid and C-domain to form heterodimers. The high Kd for capsid dimerization is not in the desired range for typical inhibitors. The sensitivity of the assembly reaction to high Kd suggests this kinetic assembly assay could be used to detect weak interacting compounds or mutants that cause only small changes in capsid-capsid interactions.

The other possibility for capsid-capsid interactions is the N-domain interactions that should only be present at high concentrations of NaCl because they are the driving forces for assembly. The C-domain interactions are not dependent upon the addition of NaCl because they are already present in solutions with low NaCl concentrations, and there is little difference between association constants in high NaCl concentrations and low NaCl concentrations. If it is assumed that the C-domain interactions formed in solution are similar to the interactions in the hexamer lattice of the tubes, then the interactions that must be formed are the N-domain interactions. This means the N-domain interaction is the necessary interaction to form cylinders. However experimental evidences for this interaction have been difficult to obtain. The capsid assembly rate was not changed in the presence of the N-domain, indicating that there is no observable interaction between the N-domain and the N-domain of the capsid protein. This is not surprising because as suggested by the difficulty to observe this interaction, the N-domain interactions are probably weak at best.

However, the N-domain was observed to affect the assembly rate when the C-domain is present. The N-domain alleviated the C-domain inhibition on capsid assembly. With the known data about the capsid assembly it is difficult to ascertain a mechanism for this alleviation caused by the N-domain. One possible mechanism is the N-domain interacts with the N-domain of capsid protein to increase the rate of nucleating assembly by increasing the concentration of the limiting component. This is ;probably unlikely because the N-domain does not affect capsid assembly unless C-domain is present. This suggests the N-domain is interacting with the C-domain during alleviation of capsid assembly.

EXAMPLE 3

Optimize Digestion Conditions and Assign Peptides Spanning the Gag Polyprotein

Since hydrogen/deuterium exchange experiments require the analysis of peptides generated from the target molecules, a library of assigned peptides for the Gag polyprotein (that is, peptides of known mass whose location in the primary sequence has been determined) need to be generated. Gag polyprotein is used because it contains all of the structural elements such as matrix, capsid, nucleocapsid and the spacer regions.

A key issue during digestion is the generation of fragments which span the entire protein. For regions in which no peptide can be identified no exchange information can be obtained. Pepsin is the enzyme of choice because it displays high activity at pH 2.5 where hydrogen/deuterium exchange in minimized, and is relatively non-specific (21). Under the acidic conditions at which digestion is performed, protein are largely unfolded rendering a large number of sites available. Digestion with pepsin typically yields fragments covering 50-80% of the protein subunit (14,15). The digestion time that yielded a reasonably large number of fragments was ~6 min. Reduction of the digestion time could reduce back exchange.

To increase the amount of digestion, the relative amount of enzyme provided can be varied and the number of fragments produced examined. Standard digestion conditions is established as the lowest concentration of enzyme required to generate all fragments. Once optimal digestion conditions is determined, and reproducibility ascertained, the peptide digests are analyzed by MALDI-TOF mass spectrometry.

Three strategies can be used for the assignment of the peptides produced. The simplest strategy is to determine if the peptide can be examined by exact mass matching. In cases where mass searching yields more than one possible peptide within a 0.3 Da mass unit window, the peptides can be identified by either postsource decay sequencing or electrospray MS/MS. In rare cases, two peptides of overlapping mass may be present in the digest, and not be resolved in the first stage MS. If required, these peptide can be separated by reverse phase HPLC prior to mass analysis. As peptides are assigned, they are mapped onto the primary sequence.

EXAMPLE 4

Determine the Alterations in the Exchange Protection Profile of the Gag Polyprotein and its Domains Accompanying Polymerization A comparative analysis of the hydrogen/deuterium exchange protection profiles of individual structural domains of the Gag polyprotein in various oligomerization states, as well as in intact monomeric Gag can be made. Wild type and mutant proteins which can be induced to polymerize into a variety of physiologically relevant morphological forms are used for comparisons. Among these comparisons are monomeric and dimeric capsid protein, spherical and cylindrical capsid polymers, CA-NC monomers and CA-NC polymers with RNA, and individual Gag domains compared to the intact polyprotein.

EXAMPLE 5

Identification of the Intersubunit Interfaces Involved in the Dimerization of Capsid Protein in Solution Monomeric wild type and mutant capsid proteins can be compared to dimeric capsid protein to characterize the dimer interface location and stability. Under low salt conditions, the capsid protein is in a monomeridimer equilibrium with an estimated $K_d$ for dimerization of between 10-30 μM (22-24). Based on this $K_d$, at concentrations above ~5 mg/ml the protein will be predominately dimeric. H/D exchange of capsid protein is therefore performed at 5-10 mg/ml protein concentration in 25 mM sodium phosphate (pH 6.5), 100 mM NaCl buffer (23).

For the exchange experiments, the first step is to establish an appropriate time scale for the CA(M185) monomer. Wild type capsid protein and the mutant CA(M185A) are exchanged at 4° C. for 5, 20, 40, 120 min and the extent of $D_2O$ exchange is examined. This straightforward experiment allows discrimination between rapidly exchanging and protected protons and map them onto the three dimensional structure. Amide H/D exchange rates at solvent accessible sites are variable but should be on the order of 0.05-4 $sec^{-1}$ (15).

In the second step, peptides which exchanged rapidly in solution and those whose exchange required large scale breathing motions are determined. The experiment described above for measuring the rate of exchange is repeated at 35° C. where breathing motions is enhanced. Distinguishing between these peptides allows one to focus on peptides which exchange without breathing motions, and therefore presumably lie on the subunit surface.

The third step is to determine the exchange rates for dimeric capsid and compare the exchange rates to those obtained for the monomer, focusing on exchange conditions chosen to favor exchange of surface residues (i.e., 4° C.). Regions which display exchange protection are identified as candidates for intersubunit interfaces. Alterations in exchange protection could also arise from conformational changes, or decreased breathing motions induced by dimerization. If regions outside of the crystallographic interface display increased exchange protection, it is likely due to conformational change. Surface amide protons should exchange on the time scale of minutes, whereas those which are buried should display slower exchange. If there is an increased protection of a peptide whose exchange rate is on the order of an hour in the monomer, it is likely that this is in the folded core of the protein. Protons with exchange rates on the order of minutes are considered good candidates for interfacial protons (15).

EXAMPLE 6

Determination of the Effect of the Matrix Capsid Junction on the Conformation of the Capsid Protein The $MA_4$-capsid dimer can be compared to dimeric capsid protein to characterize the contribution of N-terminal hairpin to capsid structure and stability. Biologically active $MA_4$-capsid protein can be obtained in sufficient quantities and at high enough concentration. These experiments are done essentially as described for the wild type capsid protein (22-24). The exchange experiments are performed essentially as described above.

EXAMPLE 7

Identification of the Differences in Capsid Protein Packing between Spherical and Cylindrical Polymers To identify the differences in subunit packing which accompany polymerization, the hydrogen/deuterium exchange protection profiles of spherical polymers assembled from $MA_4$-capsid and cylindrical polymers assembled from capsid can be compared to each other and to their constituent subunits. Comparisons of the hydrogen/deuterium exchange protection pattern within the polymer to that of the constituent subunit identify the interfacial regions formed during assembly. Comparisons of the exchange protection profile for the spherical and cylindrical forms identify the differences in the interfacial regions between the mature and immature capsid core.

The studies on spherical and cylindrical polymers can also be extended to studies of the polymerized M185A capsid mutant. This capsid mutant provides a unique opportunity to gain insight into the role of the structure of the C-terminal capsid domain in determining the morphology of the viral core. The M185A mutation disrupts the C-terminal dimer interface; however, the protein still forms polymers presumably through interactions involving only the N-terminal domain (18). Unlike the cylindrical polymers formed from the wild type capsid protein, the mutant protein polymerizes into large string-like polymers which appear to not have been able to wind up into a cylinder. Comparison of the hydrogen/deuterium exchange protection profile of these polymers to those assembled from wild type capsid protein allow separation of the contribution of the N-terminal domain towards polymerization from that of the C-terminal domain.

Capsid proteins (CA, $MA_4$-CA, and CA(M185A)) can be polymerized into tubular structures by dialysis against 1 M NaCl (18, 25, 26), and the polymerized structures are harvested by centrifugation. Exchange of the polymerized capsid can be initiated by resuspending the pelleted polymer in 1 M NaCl buffer in $D_2O$. Following exchange, the polymer is quenched and analyzed in an identical manner to that of the dimeric capsid protein. It has been reported that polymerized capsid may dissociate upon dilution (25, 26). If dissociation is slow, relative to the time of exchange, it can be safely ignored. If dissociation occurs on a time scale comparable to the time required for exchange, the rate of dissociation can be decreased with increasing salt concentration over the 1-4M NaCl range.

EXAMPLE 8

Determination of Whether the Polymers Produced by Rapid Dilution are Structurally Related to Those Produced by Dialysis High salt promotes the polymerization of capsid protein. It is well established that increasing the salt concentration rapidly (by dilution of the protein into high salt) leads to the formation of ill-formed polymers, while increasing it slowly (by dialysis) leads to relatively well formed cylindrical or spherical particles. For practical purposes, it would be advantageous to be able to trigger assembly simply by dilution of the protein into high salt. The ability to rapidly and simply trigger assembly is a prerequisite for high throughput screening of compounds designed to block key interactions during assembly. To test the hypothesis that the intersubunit interactions in polymers produced by rapid dilution may be similar to those produced by dialysis, the hydrogen/deuterium exchange protection of CA, MA4-CA, and CA(M185) in polymers produced by rapid dilution can be compared to those polymerized by dialysis.

EXAMPLE 9

Determination the Effect of RNA Dependent Polymerization on the Structure of the CA-NC Protein The hydrogen/deuterium exchange profile for monomeric CA-NC, CA-NC-p6 protein and the same proteins polymerized in the presence and absence of RNA can be determined to study the stabilization of intersubunit interactions. Raman spectroscopy can be used to detect changes in secondary structure which accompany polymerization with an eye towards identifying folding of the N- and C-terminal regions of NC upon polymerization. Biologically active CA-NC, and CA-NC-p6 are purified by the method of Campbell and Vogt (20). CA-NC is reported to remain monomeric in 1M NaCl at concentrations ~1 mg/ml in the absence of RNA (26), and at substantially higher concentration (~9 mg/ml) below 0.5 M NaCl (27). For hydrogen/deuterium exchange experiments, solvent exchange into $D_2O$ is accomplished by "spin column" desalting and followed by digestions as described above.

EXAMPLE 10

Identification of the Interactions between MA, CA, and NC Domains in the Gag Polyprotein During the lifecycle of HIV, the domains of Gag (MA, CA, and NC) exist in two distinct states, i.e. as part of the polyprotein and individually following proteolysis. Although high resolution structures exist for each of these domains individually, there is currently no data available on whether these domains interact in the intact protein and influence each others' structure, or exist as isolated domains connected by the spacer regions. Thus, the exchange protection of the capsid region of intact Gag protein can be compared to that of monomeric and dimeric capsid. Increases and decreases in the degree of protection are interpreted as evidence of either stabilizing or destabilizing interactions respectively.

EXAMPLE 11

Determination of the Dynamic Stability of Spherical and Cylindrical Polymers

Dynamic Transformations, such as protease access, maturation, and uncoating require flexibility within the viral capsid. Interfaces which stabilize the immature virion must be disrupted and new interfaces formed during maturation. Those new interfaces must subsequently dissociate during uncoating. Recent evidence using mass spectrometry and protease digestion suggests that there are substantial breathing motions within viral particles (29, 30). Destabilized regions undergoing breathing motions would appear to be good targets for antivirals.

The stability and breathing motions within spherical and cylindrical polymers of capsid protein can be examined by determining the thermal stability of the capsid protein using circular dichroism and Raman spectroscopy, and by measuring the increase in the hydrogen/deuterium exchange rates of the slowly exchanging regions of the protein with increasing temperature and GuHCl. This latter approach is an adaptation of that of Bai (10, 11) These studies will define the relative strengths of the interactions within the core of the virus, and suggest a molecular mechanism for destabilization.

EXAMPLE 12

Characterization of the Domain Interactions within Mature and Immature Budded Viral Particles The environment within the budded virus is difficult to mimic in vitro. To gain structural information about the immature and mature forms of the virion, hydrogen/deuterium exchange studies on viral particles budded from cells are performed. H/D exchange studies can be applied to enveloped viruses because the presence of the envelope itself does not interfere with hydrogen/deuterium exchange (31). Wild type and protease mutant versions of gag-pro, plasmids pTREGPCTE and pTREGP*CTE respectively, are cloned and used to produce both budded particles that are proteolytically mature or morphologically immature for comparative studies.

Stable cell lines for particle production can be created within the neomycin-resistant HeLa Tet-Off cells obtained from Clonetech. Briefly, the pTRE-based expression constructs are co-transfected into HeLa Tet-Off cells with a plasmid carrying the bygromycin resistance gene. The ratio of pTRE:Hygro plasmids is 20:1 thus ensuring that the majority of hygro-resistant clones contained the pTRE expression plasmid.

Clones are selected and then evaluated for Gag production by commercially available p24$^{CA}$ ELISA kits. Both during the hygro selection process and for culture maintenance these cells are maintained in medium containing doxycycline in order to repress expression of gag-pro. Expression of gag-pro is induced by the exchange of the culture medium with the same medium without doxycycline and containing a tet-free certified fetal bovine serum (Clonetech). Twenty-four hours post induction the culture medium is collected, filtered through a 0.45 µm filter and virus-like particles harvested by centrifugation onto a 40% w/w sucrose cushion. The medium/sucrose interface is collected, multiple samples pooled, and the pooled material made 50% w/w in sucrose. This particle/sucrose material is then used, along with a 25% w/w sucrose solution lo construct a linear 25-50% sucrose gradients in a BioComp™ gradient maker. After 16 hours of centrifugation the region of the gradients containing sucrose at a density of ~1.16 g/ml is pooled, diluted, and the virus particles pelleted. Pelleted particles are then resuspended in the appropriate buffer for H/D exchange.

The following references were cited herein:
1. Weldon, R. A., Jr., and E. Hunter. 1997. Molecular requirements for retrovirus assembly. In Structural Biology of Viruses. Oxford University Press, New York. 381-410.
2. Boulanger and Jones. 1996. *Current Topics in Microbiology and Immunology.* 214:237-260.
3. Nermut and Hockley. 1996. *Current Topics in Microbiology and Immunology.* 214:1-24.
4. Vogt. 1996. *Current Topics in Microbiology and Immunology.* 214:95-131.
5. Englander et al. 1979. *Analytical Biochemistry.* 92:517-524.
6. Woodward. 1994. *Current Opinion in Structural Biology.* 4:112-116.
7. Dill. 1990. *Biochemistry.* 29:7133-7155.
8. Englander and Mayne. 1992. *Annu. Rev. Biophys. Biomol. Struct.* 21:243-265.
9. Englander et al. 1996. *Current Opinion in Structural Biology.* 6:18-23.
10. Bai et al. 1994. *Proteins: Structure, Function, and Genetics.* 20:4-14.
11. Bai et al. 1995. *Science.* 269:192-197.
12. Tuma and Thomas, Jr. 1996. *Biophysical Journal.* 71:3454-3466.
13. Dharmasiri and Smith. 1996. *Analytical Chemistry.* 68:2340-4.
14. Mandell et al. 1998. *Anal Chem.* 70:3987-95.
15. Mandell et al. 1998. *Proc Natl Acad Sci USA.* 95:14705-10.
16. Ohguro et al. 1994. *Protein Science.* 3:2428-34.
17. Smith et al. 1997. *Journal of Mass Spectromietry.* 32:135-46.
18. von Schwedler et al. 1998. *EMBO J.* 17:1555-1568.
19. Brinkmann et al. 1989. *Gene.* 85:109-14.
20. Campbell and Vogt. 1995. *J Virol.* 69:6487-6497.
21. Juhasz and Martin. 1997. *Int. J. Mass Spectrom. Ion Processes.* 169:217-230.
22. Rose et al. 1992. *Proteins.* 13:112-119.
23. Yoo et al. 1997. *J Mol Biol.* 269:780-795.
24. Brooks et al. 1994. *Methods Enzymol.* 240:459-478.
25. Ehrlich et al. 1992. *J Virol.* 66:4874-83.
26. Gross et al. 1997. *Eur J Biochem.* 249:592-600.
28. Ganser et al. 1999. *Science.* 283:80-3.
29. Bothner et al. 1998. *J Biol Chem.* 273:673-676.
30. Lewis et al. 1998. *Proc Natl Acad Sci USA.* 95:6774-8.
31. Tuma et al. 1996. *Journal of Molecular Biology.* 257: 102-115.

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for a compound that modulates viral assembly and maturation comprising the steps of:
   maintaining a human immunodeficiency virus type 1 (HIV-1) capsid protein in solution;
   rapidly increasing salt concentration in said solution in the presence of a candidate compound or a control compound, wherein said HIV-1 capsid protein is capable of self-assembling upon said salt concentration increase in the presence of said control compound but not said candidate compound, and wherein said solution after said salt concentration increase comprises at least 1 M sodium salt; and
   monitoring assembly of said HIV-1 capsid protein in the presence of said candidate compound, wherein an increase or decrease of assembly of said HIV-1 capsid protein in the presence of said candidate compound compared to said control compound indicates said candidate compound promotes or inhibits HIV-1 assembly respectively.

2. The method of claim 1, wherein said HIV-1 capsid protein is maintained in a soluble form through the use of an anti-aggregation agent.

3. The method of claim 2, wherein said anti-aggregation agent is GuHCl.

4. The method of claim 3, wherein said GuHCl is in a concentration of from about 1 M to about 6 M.

5. The method of claim 1, wherein said candidate compound is selected from the group consisting of protein, peptide derived from the HIV-1 Gag polyprotein and a non-peptide small molecule.

6. The method of claim 1, wherein said monitoring of HIV-1 capsid protein assembly is by a method selected from the group consisting of measuring turbidity, measuring fluorescence and physical separation of the polymerized viral protein.

7. A method of screening for agents capable of inhibiting HIV assembly and maturation, said method comprising:
   maintaining a polypeptide in a soluble form, said polypeptide comprising an HIV capsid protein;
   diluting said polypeptide in a high salt solution in the presence of a molecule of interest, wherein said polypeptide is capable of self-assembling upon dilution in said high salt solution in the absence of said molecule of interest and wherein the final concentration of said high salt solution is at least 1 M sodium salt; and
   monitoring assembly of said polypeptide in the presence of said molecule of interest,
   wherein a decrease in the assembly of said polypeptide in the presence of said molecule of interest as compared to that in the absence of said molecule of interest indicates that said molecule is capable of inhibiting HIV assembly and maturation.

8. The method of claim 7, wherein said polypeptide consists essentially of the HIV capsid protein.

9. The method of claim 7, wherein said polypeptide is maintained in a solution comprising from about 1 M to about 6 M GuHCl before said diluting.

10. A method of screening for agents capable of inhibiting HIV assembly and maturation, said method comprising:
    maintaining a polypeptide in a soluble form, said polypeptide comprising an HIV capsid protein;
    rapidly mixing said polypeptide with a high salt solution in the presence of a molecule of interest, wherein said mixing is capable of triggering assembly of said polypeptide in the absence of said molecule of interest and wherein the final concentration of said high salt solution is at least 1 M sodium salt; and
    monitoring assembly of said polypeptide in the presence of said molecule of interest,
    wherein a decrease in the assembly of said diluted polypeptide in the presence of said molecule of interest as compared to that in the absence of said molecule indicates that said molecule is capable of inhibiting HIV assembly and maturation.

11. The method of claim 10, wherein said polypeptide is maintained in a solution comprising from about 1 M to about 6 M GuHCl before said mixing.

12. A method for identifying modulators of human immunodeficiency virus (HIV) assembly and maturation, comprising the steps of:
    maintaining an HIV capsid (CA) protein in a solution;
    rapidly mixing a said solution comprising said HIV CA protein with a high salt solution in the presence of an agent of interest, wherein the resulting solution after said mixing comprises at least 1 M sodium salt, and
    monitoring assembly of said HIV capsid protein after said mixing,
    wherein a change in the assembly of said HIV capsid protein in the presence of said agent as compared to that in the absence if said agent indicates that said agent is a modulator of HIV assembly and maturation.

* * * * *